United States Patent
Hyeong et al.

(10) Patent No.: US 12,286,388 B2
(45) Date of Patent: Apr. 29, 2025

(54) 1,5,9-CYCLODODECATRIENE COMPOSITION AND CONTINUOUS PREPARATION METHOD THEREFOR

(71) Applicant: HANWHA SOLUTIONS CORPORATION, Seoul (KR)

(72) Inventors: Seonghoon Hyeong, Daejeon (KR); Jinho Park, Daejeon (KR); Namjin Jang, Daejeon (KR)

(73) Assignee: HANWHA SOLUTIONS CORPORATION, Seoul (KR)

(*) Notice: Subject to any disclaimer, the term of this patent is extended or adjusted under 35 U.S.C. 154(b) by 91 days.

(21) Appl. No.: 18/034,140

(22) PCT Filed: Oct. 27, 2021

(86) PCT No.: PCT/KR2021/015178
§ 371 (c)(1),
(2) Date: Apr. 27, 2023

(87) PCT Pub. No.: WO2022/092794
PCT Pub. Date: May 5, 2022

(65) Prior Publication Data
US 2023/0399273 A1    Dec. 14, 2023

(30) Foreign Application Priority Data
Oct. 27, 2020 (KR) .................. 10-2020-0140015

(51) Int. Cl.
C07C 2/46     (2006.01)
C07C 13/277   (2006.01)

(52) U.S. Cl.
CPC .............. *C07C 2/46* (2013.01); *C07C 13/277* (2013.01)

(58) Field of Classification Search
CPC .............................. C07C 13/277; C07C 2/46
See application file for complete search history.

(56) References Cited

U.S. PATENT DOCUMENTS

3,636,174 A * 1/1972 Nakamura et al. .. B01J 31/0212
585/367
2007/0265184 A1   11/2007 Herwig et al.

FOREIGN PATENT DOCUMENTS

| CN | 105693455 A | 6/2016 |
| JP | 05-124982 A | 5/1993 |
| JP | 2003-335709 A | 11/2003 |
| JP | 2005-139144 A | 6/2005 |
| JP | 2015-533628 A | 11/2015 |

(Continued)

OTHER PUBLICATIONS

Communication dated Mar. 19, 2024, issued in Japanese Application No. 2023-525477.

(Continued)

*Primary Examiner* — Sharon Pregler
(74) *Attorney, Agent, or Firm* — Saghrue Mion, PLLC

(57) ABSTRACT

The present invention provides a continuous preparation method of cyclododecatriene including: preparing a reaction composition by mixing butadiene, a main catalyst, and a co-catalyst with a toluene solvent; and allowing the reaction composition to react at a reaction pressure higher than a vapor pressure of the butadiene, and a cyclododecatriene composition prepared by the continuous preparation method.

12 Claims, 2 Drawing Sheets

(56) References Cited

FOREIGN PATENT DOCUMENTS

KR     10-2011-0122327 A     11/2011

OTHER PUBLICATIONS

Office Action issued Sep. 3, 2024 in Japanese Application No. 2023-525477.
Extended European Search Report issued Sep. 4, 2024 in European Application No. 21886788.5.
Da Min Park et al., Synthesis of Cyclododecatriene from 1,3-Butadiene by Trimerization over Amine-Titanium Complex Catalyst, Department of Chemical Engineering, Inha University, Jun. 2013, pp. 394-402, vol. 51, No. 3.
International Search Report for PCT/KR2021/015178 dated Feb. 9, 2022.

* cited by examiner

1,5,9-CYCLODODECATRIENE COMPOSITION AND CONTINUOUS PREPARATION METHOD THEREFOR

This Application is a National Stage of International Application No. PCT/KR2021/015178 filed Oct. 27, 2021, claiming priority based on Korean Patent Application No. 10-2020-0140015 filed Oct. 27, 2020.

TECHNICAL FIELD

The present invention relates to a 1,5,9-cyclododecatriene composition and a continuous preparation method of the same.

BACKGROUND ART 1,5,9-Cyclododecatriene (CDT) has been efficiently used as an intermediate in producing an organic compound such as a lactam compound, a polyamide compound, or a dicarboxylic acid. 1,5,9-Cyclododecatriene may be synthesized by a cyclotrimerization reaction of 1,3-butadiene. Such a cyclotrimerization reaction generally proceeds by mixing 1, 3-butadiene, a catalyst, and the like with a solvent, and the solvent used for the reaction is specifically hexane, heptane, octane, decane, cyclohexane, cyclooctane, cyclodecane, cyclododecane, benzene, toluene, xylene, or the like. In the related art, benzene has been generally used as a solvent, but benzene is a first-class carcinogen, which is harmful to the human body and is not easy to handle. Therefore, there is a need for a substance to replace it. Toluene having physical properties similar to those of benzene is highly harmful to the human body like benzene, but is relatively easy to handle. However, in the case of using toluene as a solvent, it was analyzed that new by-products different from the by-products produced as a reaction proceeded in the conventional benzene solvent were produced, and typically, a toluene-$C_4$ complex was produced in excess, resulting in a significant decrease in CDT selectivity.

In addition, although not standing out when the reaction proceeded at the conventional laboratory level or in a batch reactor or a continuous stirred tank reactor (CSTR), which is one type of reactor, a foaming phenomenon occurred in the reactor in a situation where mass production was required, such as a commercial process of CDT, resulting in a significant decrease in conversion.

Therefore, optimized reactor operating conditions have been required to suppress by-products such as toluene-$C_4$ produced as the cyclotrimerization reaction proceeds using a toluene solvent and to improve CDT conversion and yield by suppressing a foaming phenomenon that occurs in a commercialization process of mass-producing CDT.

DISCLOSURE

Technical Problem

In the present invention, in a method for continuously producing CDT, it is intended to suppress production of by-products such as 4-vinylcyclohexane (VCH), cyclooctadiene (COD), and a toluene-$C_4$ complex.

In addition, it is intended to suppress a foaming phenomenon that occurs in a commercialization process of mass-producing CDT.

In addition, optimized process operating conditions may be suggested to improve a conversion and yield of CDT products.

Technical Solution

In one general aspect, a continuous preparation method of cyclododecatriene includes: preparing a reaction composition by mixing butadiene, a main catalyst, and a co-catalyst with a toluene solvent; and allowing the reaction composition to react at a reaction pressure higher than a vapor pressure of the butadiene.

The main catalyst may be one or more of titanium chloride and titanium alkoxide.

A concentration of the main catalyst in the reaction composition may be more than 0.5 mmol/L and less than 2.5 mmol/L.

The main catalyst and the co-catalyst may be mixed so that an aluminum/titanium (Al/Ti) mole ratio is 10 to 100.

The butadiene may be mixed in a liquid state.

The butadiene and the toluene solvent may be included at a weight ratio of 1:1 to 3:1.

The reaction pressure may be 5 to 10 bar.

In the continuous preparation method, the reaction composition may be allowed to react at a reaction temperature of 30 to 70° C.

In the continuous preparation method, the reaction composition may be allowed to react for 30 to 80 minutes.

In another general aspect, there is provided a cyclododecatriene composition prepared by the continuous preparation method, wherein a conversion of the butadiene is 85 wt % or more and a selectivity of the cyclododecatriene is 85 wt % or more.

The cyclododecatriene composition may have a 4-vinylcyclohexane (VCH) selectivity of less than 1 wt %.

The cyclododecatriene composition may have a cyclooctadiene (COD) selectivity of less than 0.2 wt %.

The cyclododecatriene composition may have a toluene-$C_4$ (Tol-$C_4$) selectivity of less than 15 wt %.

Advantageous Effects

As set forth above, the production of by-products such as toluene-$C_4$ may be suppressed, and the foaming phenomenon that occurs in the commercialization process of mass-producing CDT may be suppressed, thereby improving CDT conversion and yield.

BEST MODE

Figure 1:
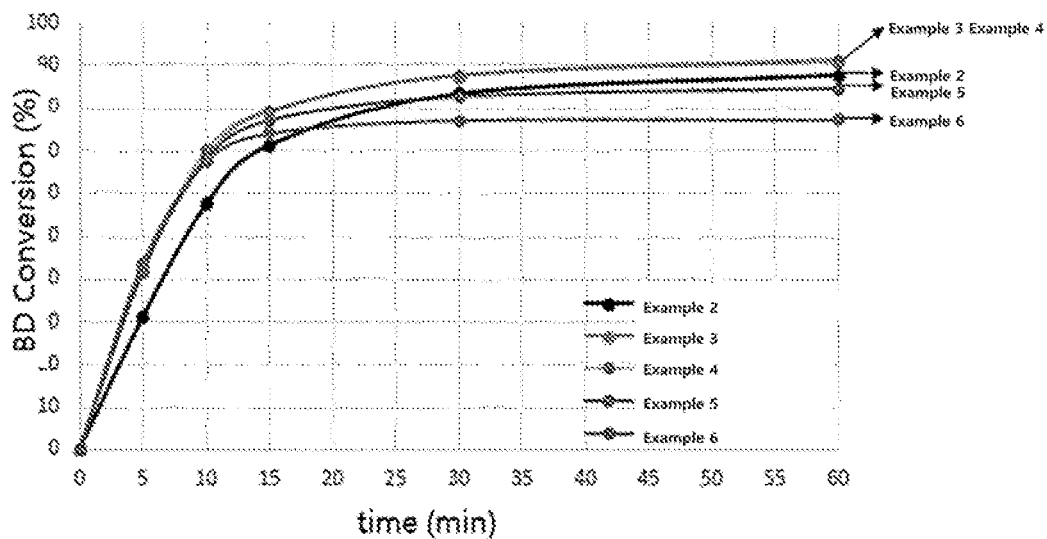
FIG. 1 is a graph comparing butadiene conversions by concentration of a main catalyst according to Examples 2 to 6.

A continuous preparation method of cyclododecatriene (1,5,9-CDT) according to the present invention will be described below, but technical terms and scientific terms used herein have the general meanings understood by those skilled in the art to which the present invention pertains unless otherwise defined, and descriptions of the known function and configuration unnecessarily obscuring the gist of the present invention will be omitted in the following description.

Focusing on the problems of the related art described above, the present invention intends to suggest a continuous preparation method of cyclododecatriene capable of realizing a high conversion and selectivity in a significantly economical manner.

Unless otherwise specified in the present specification, butadiene may refer to 1,3-butadiene.

In addition, toluene may be contained in a toluene solvent in an amount of 90 vol % or more, preferably 95 vol % or more, and more preferably 99 vol % or more, with respect to the total volume of the solvent.

In addition, a CDT selectivity, a VCH selectivity, a COD selectivity, and a toluene-$C_4$ selectivity (wt %) in a cyclododecatriene composition may refer to contents (wt %) in the cyclododecatriene composition, respectively.

In addition, A to B may refer to a range of A or more and B or less.

In addition, it is to be understood that the term "comprising" described in the present specification does not exclude other components, and may further include other components that are not mentioned.

Hereinafter, there is provided a continuous preparation method of cyclododecatriene (CDT) according to an embodiment. The continuous preparation method includes: preparing a reaction composition by mixing butadiene, a main catalyst, and a co-catalyst with a toluene solvent; and allowing the reaction composition to react at a reaction pressure higher than a vapor pressure of the butadiene.

The reaction composition may contain butadiene and toluene at a weight ratio of 1:1 to 3:1, for example, 1:1 to 2:1, and preferably 1:1 to 1.5:1. The present invention is a commercial process in which a reaction proceeds continuously as mass production of CDT is required, and the butadiene and toluene are mixed in the reaction composition at the above content ratio. As the butadiene is injected in excess, a foaming phenomenon occurs in the reactor. It is considered that, in such a foaming phenomenon, as a cyclotrimerization reaction of butadiene proceeds, the temperature in the reactor rapidly increases and phase transitions such as boiling of butadiene occur, which causes a decrease in conversion as a result of blocking contact between the catalyst and butadiene, generation of a dead zone in the reactor, an increase in space velocity of the reaction composition, and the like.

However, when process operating conditions of the present invention, such as a reaction pressure and a reaction temperature of a continuous reactor, a space velocity of the reaction composition, and a combination of reactors, are applied, butadiene as the reaction composition may be injected in an amount equal to or more than the weight of the toluene solvent, and the foaming phenomenon is suppressed, such that a significantly excellent butadiene conversion, CDT selectivity, and CDT yield may be obtained. For example, when the weight ratio of butadiene to toluene is less than 1:1, the CDT yield is not sufficiently secured, and when the weight ratio exceeds 3:1, the butadiene conversion is decreased, and it is not easy to optimize the operating conditions of the reactor, resulting in an increase in additional operating costs due to occurrence of sludge.

When toluene is used as a solvent for the cyclotrimerization reaction, as described above, toluene has physical properties similar to those of conventionally used benzene, yet it is easy to handle, has a low harmfulness to the human body, and is readily available. However, 4-vinylcyclohexane (VCH), cyclooctadiene (COD), a polymer, 1-phenyl butane (PhB), and the like are reported as by-products produced when a benzene solvent is used, but when the toluene solvent of the present invention is used, in addition to 4-vinylcyclohexane (VCH) and cyclooctadiene (COD), a toluene-$C_4$ complex is produced in excess, resulting in a significant decrease in CDT selectivity. However, when the process operating conditions of the present invention, such as the reaction pressure and the reaction temperature of the CSRT reactor, the space velocity of the reaction composition, the combination of reactors, are applied, the production of the toluene-$C_4$ complex may be suppressed.

The main catalyst may include one or more of titanium chloride and titanium alkoxide, and the co-catalyst may include organic aluminum, for example, one or more of ethoxy diethyl aluminum, diethyl aluminum chloride, and ethyl aluminum sesquichloride (EASC). Preferably, titanium tetrachloride ($TiCl_4$) or titanium alkoxide may be used as the main catalyst, and ethoxy diethyl aluminum or EASC may be used as the co-catalyst, but the present invention is not limited thereto.

The main catalyst may be contained in an amount of 0.001 to 0.1 wt %, for example, 0.01 to 0.1 wt %, preferably 0.01 to 0.07 wt %, and more preferably 0.01 to 0.05 wt % or 0.01 to 0.04 wt %, with respect to the total weight of the reaction composition. In addition, a concentration of the main catalyst in the reaction composition may be more than 0.5 mmol/L and less than 2.5 mmol/L, preferably 0.6 to 2 mmol/L or 0.6 to 1.5 mmol/L, more preferably 0.6 to 1.3 mmol/L or 0.7 to 1.1 mmol/L, and most preferably 0.6 to 1 mmol/L or 0.7 to 0.9 mmol/L.

When the content of the main catalyst is too low, it is difficult to provide active sites, such that the cyclotrimerization reaction of butadiene cannot proceed sufficiently, and when an excessive amount of the main catalyst is included, the temperature of the reactor rapidly increases, such that the production of the by-products is accelerated and sludge may be accumulated in the reactor.

The co-catalyst may be contained in an amount of 0.01 to 5 wt %, for example, 0.1 to 5 wt %, preferably 0.5 to 5 wt %, and more preferably 1 to 3 wt %, with respect to the total weight of the reaction composition, but the present invention is not limited thereto.

The main catalyst and the co-catalyst may be contained in the reaction composition so that an aluminum/titanium (Al/Ti) mole ratio is 10 to 100, preferably 20 to 80 or 30 to 70, and more preferably 35 to 65 or 40 to 60. In general, it is known that the CDT selectivity and the butadiene conversion are decreased when the aluminum/titanium mole ratio in the main catalyst and the co-catalyst is 15 to 20 or more (reference, Korean Chem. Eng. Res., 51(3), 394-402 (2013), Synthesis of Cyclododecatriene from 1,3-Butadiene by Trimerization over Amine-Titanium Complex Catalyst, table 2), but in the reaction conditions of the present invention, it is possible to obtain a more excellent CDT selectivity and butadiene conversion in the above numerical ranges, and therefore, the amount of main catalyst used may be reduced, and a regeneration process of the main catalyst may be simplified, which is preferable for improving process efficiency.

The reaction proceeds at a reaction pressure higher than a vapor pressure of the butadiene. Accordingly, the butadiene may be injected in a liquid state, and may be injected in the same weight or excessive weight compared to toluene, which is a solvent. For example, when the reaction pressure is lower than the vapor pressure of the butadiene, the foaming phenomenon occurs in the reactor, which may decrease the butadiene conversion and may decrease the CDT selectivity, and when the reaction pressure is excessively high, the CDT selectivity may be decreased.

Specifically, the cyclotrimerization polymerization reaction of the butadiene may proceed at a reaction temperature of 30 to 70° C., preferably 40 to 60° C., more preferably 45 to 55° C., and a reaction pressure of 5 to 10 bar, preferably 5 to 9 bar, and more preferably 5 to 7 bar or 5 to 6 bar.

In the cyclotrimerization reaction, the temperature increases by 30 to 50° C. from the initial temperature of 25° C. (room temperature) in the reactor and maintained within the above reaction temperature range. When the reaction temperature is too low, the catalytic activity is poor, resulting in a low butadiene conversion, and when the reaction temperature is excessively high, the foaming phenomenon occurs, which may decrease the butadiene conversion and may increase the selectivity of VCH among the by-products.

The cyclotrimerization polymerization reaction of the butadiene may proceed under the above reaction temperature and reaction pressure conditions for 30 to 80 minutes and preferably 40 to 70 minutes, but the present invention is not limited thereto.

Meanwhile, the cyclotrimerization polymerization reaction of the butadiene may proceed in at least one selected from a continuous stirred tank reactor (CSTR) and a plug flow reactor (PFR), and is thus characterized by continuously producing CDT.

CSTR, one of the continuous reactors, has an advantage in that a uniform temperature is maintained during the reaction and a probability of generating a local hot spot is low because the reaction composition may be continuously injected and a mixing effect may be provided during the reaction, but has a disadvantage in that a conversion of the reaction composition per reactor volume is low, and a molecular weight distribution of the reaction product is widened due to the remaining polymer that is not discharged within the plateau time.

In addition, PFR, one of the other continuous reactors, is relatively easy to maintain and has a high conversion per reactor volume because there is no stirring, but it is difficult to control the temperature in the reactor, and there is a high probability of generating a local hot spot when the reaction is an exothermic reaction.

However, according to an embodiment of the present invention, production of by-products such as widening of the molecular weight distribution is suppressed while maintaining high CDT productivity, such that a high CDT selectivity and butadiene conversion may be achieved, thereby implementing optimized continuous CDT production with high efficiency.

Another embodiment of the present invention provides a cyclododecatriene composition prepared by the continuous preparation method of cyclododecatriene and having the following physical properties.

The cyclododecatriene composition may have a butadiene (BD) conversion of 85 wt % or more, 87 wt % or more, 90 wt % or more, or 95 wt % or more.

The cyclododecatriene composition may have a cyclododecatriene (CDT) selectivity (content) of 85 wt % or more, 87 wt % or more, 90 wt % or more, 91 wt % or more, 92 wt % or more, 95 wt % or more, or 97 wt % or more.

The cyclododecatriene composition may have a 4-vinylcyclohexane (VCH) selectivity (content) of less than 1 wt %, less than 0.8 wt %, less than 0.5 wt %, or less than 0.3 wt %.

The cyclododecatriene composition may have a cyclooctadiene (COD) selectivity (content) of less than 0.2 wt %, less than 0.19 wt %, less than 0.18 wt %, less than 0.17 wt %, less than 0.15 wt %, less than 0.14 wt %, or less than 0.13 wt %.

The cyclododecatriene composition may have a toluene-$C_4$ (Tol-$C_4$) selectivity (content) of less than 15 wt %, less than 13 wt %, less than 11 wt %, less than 9 wt %, less than 7 wt %, less than 5 wt %, less than 3 wt %, or less than 1 wt %.

Therefore, the production of by-products such as toluene-$C_4$ may be suppressed, and the foaming phenomenon that occurs in a commercialization process of mass-producing CDT may be suppressed, thereby improving CDT conversion and yield.

Hereinafter, Examples according to an embodiment will be described. However, it is obvious that Examples are provided to better understand the description of the present invention by describing an embodiment of the present invention in detail, and the scope of the present invention is not limited thereto.

EXAMPLES

Example 1

A CSTR reaction with one batch of 200 g of toluene, 200 g of 1, 3-butadiene, 1 mmol/L of $TiCl_4$, and EASC with a mole ratio of 56 (Al/Ti=56) proceeded in a 0.6 L reactor in at least three batches. The CSTR operating conditions were 50° C. and 5 bar, the plateau time was 20 minutes per batch, and the stirring speed was fixed at 500 rpm. The reaction product was subjected to gas chromatography (GC) analysis to calculate selectivity and butadiene conversion. In addition, the occurrence of sludge inside CSTR was visually confirmed. The results are shown in Table 1.

EVALUATION EXAMPLES

Evaluation Example 1: Evaluation of Butadiene Conversion and Occurrence of Sludge According to Change in Reaction Pressure in CSTR Comparative Example 1

A process was performed in the same manner as that of Example 1, except that the CRTR operating conditions were 50° C. and 1.5 bar.

TABLE 1

| | Selectivity (wt %) | | | | Butadiene Conversion | Occurrence |
| --- | --- | --- | --- | --- | --- | --- |
| | CDT | VCH | COD | Tol-$C_4$ | (wt %) | of Sludge |
| Comparative Example 1 | 29.10 | 11.78 | 1.15 | 57.66 | 10 | ◉ |
| Example 1 | 97.71 | 1.20 | 0.14 | 0.95 | 95 | X |

(Evaluation of occurrence of sludge, ◉: occurrence of sludge, ○: occurrence of small amount of sludge, X: no occurrence of sludge)

1,3-Butadiene was injected in a liquid state, the boiling point was −4.4° C., the vapor pressure was 20° C. at 2.5 bar, and the reaction conditions were 50° C. and 5.7 bar. Referring to Table 1, it was confirmed that the CDT yield and selectivity were secured when the reaction proceeded at a reaction pressure higher than the vapor pressure. These results are analyzed to be due to suppression of evaporation of 1,3-butadiene and foaming.

In addition, toluene used as a solvent has physical properties similar to those of benzene, yet it is easy to handle, has a low harmfulness to the human body compared to a conventional benzene solvent, and is readily available. However, in the case of Comparative Example 1, a toluene-$C_4$ complex was produced in excess as a reaction by-product, resulting in a significant decrease in CDT selectivity. On the other hand, in the case of Example 1, as the CDT production reaction proceeded at a reaction pressure higher than the vapor pressure of butadiene, the production of toluene-$C_4$ was suppressed.

Evaluation Example 2: Evaluation of Butadiene Conversion and Selectivity of Reaction Product by Concentration of Main Catalyst Examples 2 to 5

Processes were performed in the same manner as that of Example 1, except that the concentration of the main catalyst and the concentration of the co-catalyst were the same as shown in Table 2. The reaction products of Examples 2 to 6 were subjected to gas chromatography (GC) analysis to calculate selectivity and butadiene conversion. The results are illustrated in FIGS. 1 to 4.

TABLE 2

|  | Example 2 | Example 3 | Example 4 | Example 5 | Example 6 |
|---|---|---|---|---|---|
| Main Catalyst Concentration ($TiCl_4$, mmol/L) | 0.5 | 0.75 | 1 | 2.5 | 5 |
| Co-catalyst Concentration (mole ratio [Al/Ti]) |  |  | 50 |  |  |

FIG. 1 is a graph comparing butadiene conversions by concentration of the main catalyst. Referring to FIG. 1, in Examples 3 and 4, the butadiene conversion was improved to 90% or more, in Example 2, the butadiene conversion was deteriorated to less than 90%, and in Examples 5 and 6, the butadiene conversion was deteriorated to less than 85%. From this, it could be confirmed that a preferred range of the concentration of the main catalyst was 0.75 to 1 mmol/L. It is analyzed that this result is because when the concentration of the main catalyst is less than 0.75 mmol/L, sufficient active sites are not provided, which makes it difficult to allow the cyclotrimerization reaction of butadiene to proceed, and when the concentration of the main catalyst exceeds 1 mmol/L, the temperature of the reactor rapidly increases.

Figure 2:
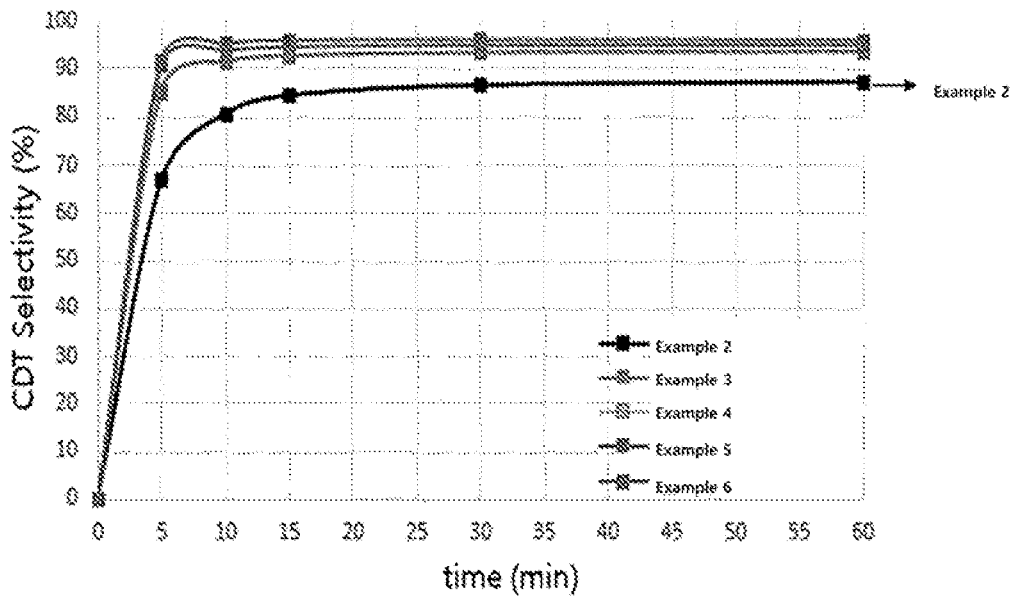
FIG. 2 is a graph comparing CDT selectivities by concentration of the main catalyst according to Examples 2 to 6.

FIG. 2 is a graph comparing CDT selectivities by concentration of the main catalyst. Referring to FIG. 2, in Examples 3 to 6, the CDT selectivity was 90% or more, which was high, and it could be confirmed that a preferred range of the concentration of the main catalyst was 0.75 mmol/L.

Figure 3:
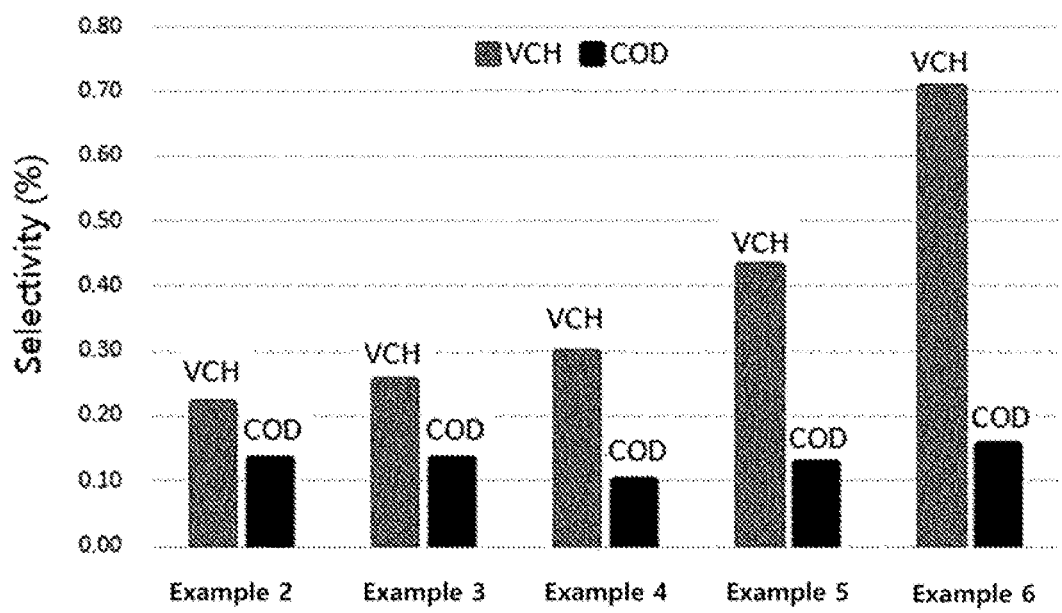
FIGS. 3 and 4 are graphs comparing selectivities of reaction by-products (VCH, COD, and Tol-$C_4$) by concentration of the main catalyst according to Examples 2 to 6.
Figure 4:
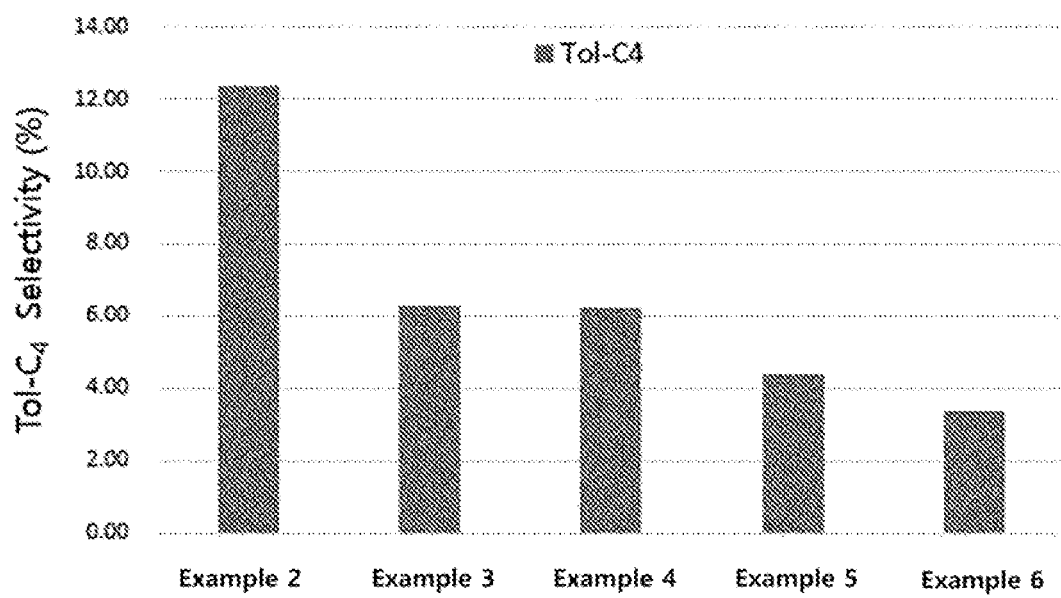

FIGS. 3 and 4 are graphs comparing selectivities of reaction by-products (VCH, COD, and Tol-$C_4$) by concentration of the main catalyst.

Referring to FIG. 3, it was analyzed that, in the case of VCH, the selectivity was increased in proportion to the concentration of the catalyst, and in the case of COD, the selectivity was hardly changed within the entire concentration range.

Referring to FIG. 4, it was analyzed that, in the case of Tol-$C_4$, the selectivity was inversely proportional to the concentration of the catalyst, and there was no significant difference in the yield at 0.75 to 1 mmol/L.

From the results of Table 2 and FIGS. 1 to 4, it could be appreciated that the concentration of the main catalyst for the optimal reactivity of the cyclotrimerization reaction of butadiene was more than 0.5 mmol/L and less than 1 mmol/L and preferably 0.75 mmol/L.

Evaluation Example 3: Evaluation of Butadiene Conversion and Selectivity of Reaction Product by Concentration (Al/Ti Mole Ratio) of Co-Catalyst Examples 7 to 9

The cyclotrimerization reaction of butadiene by EASC concentration (Al/Ti mole ratio) of the co-catalyst at the optimal concentration of the main catalyst of 0.75 mmol/L proceeded for 60 minutes. The results are shown in Table 3.

TABLE 3

|  | Example 7 | Example 8 | Example 9 |
|---|---|---|---|
| Al/Ti ratio (mole ratio) | 30 | 50 | 70 |
| BD Conversion (wt %) | 91.38 | 91.25 | 85.19 |
| CDT Selectivity (wt %) | 86.88 | 93.35 | 92.29 |
| VCH Selectivity (wt %) | 0.21 | 0.25 | 0.25 |
| COD Selectivity (wt %) | 0.19 | 0.13 | 0.12 |
| Tol-$C_4$ Selectivity (wt %) | 12.71 | 6.27 | 7.34 |

From the results of Table 3, it could be appreciated that the concentration of the co-catalyst for the optimal reactivity of the cyclotrimerization reaction of butadiene was an Al/Ti mole ratio of 30 to 70 and preferably 40 to 60.

Hereinabove, although the present invention has been described by specific matters and limited embodiments, they have been provided only for assisting in the entire understanding of the present invention. Therefore, the present invention is not limited to the embodiments. Various modifications and changes may be made by those skilled in the art to which the present invention pertains from this description. Therefore, the spirit of the present invention should not be limited to the described embodiments, but the claims and all modifications equal or equivalent to the claims are intended to fall within the spirit of the present invention.

The invention claimed is:

1. A continuous preparation method of cyclododecatriene comprising:
    preparing a reaction composition by mixing butadiene, a main catalyst, and a co-catalyst with a toluene solvent; and
    reacting the reaction composition at a reaction pressure higher than a vapor pressure of the butadiene in a temperature range of 30 to 70° C.

2. The continuous preparation method of cyclododecatriene of claim 1, wherein the butadiene and the toluene solvent are included at a weight ratio of 1:1 to 3:1.

3. The continuous preparation method of cyclododecatriene of claim 1, wherein the main catalyst is one or more of titanium chloride and titanium alkoxide.

4. The continuous preparation method of cyclododecatriene of claim 1, wherein a concentration of the main catalyst in the reaction composition is more than 0.5 mmol/L and less than 2.5 mmol/L.

5. The continuous preparation method of cyclododecatriene of claim 1, wherein the main catalyst and the co-catalyst are mixed so that an aluminum/titanium (Al/Ti) mole ratio is 10 to 100.

6. The continuous preparation method of cyclododecatriene of claim 1, wherein the butadiene is mixed in a liquid state.

7. The continuous preparation method of cyclododecatriene of claim 1, wherein the reaction pressure is 5 to 10 bar.

8. The continuous preparation method of cyclododecatriene of claim 1, wherein the reaction composition is reacted for 30 to 80 minutes.

9. A cyclododecatriene composition prepared by the continuous preparation method of cyclododecatriene of claim 1, wherein a conversion of the butadiene is 85 wt % or more and a selectivity of the cyclododecatriene is 85 wt % or more.

10. The cyclododecatriene composition of claim 9, wherein the cyclododecatriene composition has a 4-vinylcyclohexane (VCH) selectivity of less than 1 wt %.

11. The cyclododecatriene composition of claim 9, wherein the cyclododecatriene composition has a cyclooctadiene (COD) selectivity of less than 0.2 wt %.

12. The cyclododecatriene composition of claim 9, wherein the cyclododecatriene composition has a toluene-$C_4$ (Tol-$C_4$) selectivity of less than 15 wt %.

\* \* \* \* \*